United States Patent [19]

Ploog et al.

[11] Patent Number: 4,670,253

[45] Date of Patent: Jun. 2, 1987

[54] METHOD AND COMPOSITION FOR INCREASING WET HAIR COMBABILITY

[75] Inventors: Uwe Ploog, Haan; Peter Busch, Erkrath-Unterbach; Hermann Hensen, Hilden; Klaus Thiele, Langenfeld, all of Fed. Rep. of Germany

[73] Assignee: Henkel Kommanditgesellschaft auf Aktien, Duesseldorf, Fed. Rep. of Germany

[21] Appl. No.: 700,419

[22] Filed: Feb. 11, 1985

[30] Foreign Application Priority Data

Mar. 16, 1984 [DE] Fed. Rep. of Germany ....... 3409634

[51] Int. Cl.$^4$ .................. A61K 7/06; A61K 7/09; A61K 7/135
[52] U.S. Cl. ................. 424/70; 424/DIG. 2; 424/62; 424/72
[58] Field of Search ................ 558/197, 198; 424/70

[56] References Cited

U.S. PATENT DOCUMENTS

| 2,683,168 | 7/1954 | Jensen et al. | 260/953 |
| 4,440,743 | 4/1984 | Faucher | 424/70 |

FOREIGN PATENT DOCUMENTS

| 0077920 | 5/1983 | European Pat. Off. | 424/70 |
| 605984 | 11/1934 | Fed. Rep. of Germany | 424/70 |
| 1214229 | 11/1962 | Fed. Rep. of Germany | . |
| 1264687 | 3/1968 | Fed. Rep. of Germany | 424/70 |
| 3027943 | 2/1981 | Fed. Rep. of Germany | 424/70 |
| 48-11955 | 4/1973 | Japan | 424/70 |
| 48-29141 | 9/1973 | Japan | 424/70 |
| 0124712 | 9/1980 | Japan | 424/70 |
| 0077219 | 6/1981 | Japan | 424/70 |
| 2028133 | 3/1980 | United Kingdom | 424/70 |

OTHER PUBLICATIONS

G. M. Kosolapoff, J. Am. Chem. Soc. 75 (1953) pp. 1500–1501.
W. Fossek, Monatshefte fuer Chemie, vol. 7 (1886) pp. 20–39.
B. Blaser, Zeitschrift fuer anorganische und allgemeine Chemie, vol. 381, 247–259.
W. Ploeger, Zeitschrift fuer anorganische & allgemeine Chemie, vol. 389, 119–128.
Chemical Abstracts, 1977, vol. 86, p. 92239m, Aminor et al.
Chemical Abstract, 1979, vol. 90, p. 24731y, Cuntze.
Chemical Abstracts, 1973, vol. 78, p. 60541x, Schlicht.
Chemical Abstracts, 1977, vol. 86, p. 91694u.

*Primary Examiner*—Dale R. Ore
*Attorney, Agent, or Firm*—Ernest G. Szoke; Henry E. Millson, Jr.; Mark A. Greenfield

[57] ABSTRACT

Phosphonic acid esters obtained by reacting organophosphonic acids corresponding to the general formula $R-PO_3H_2$, in which R is preferably an alkyl group containing from 6 to 18 C-atoms, with from 1 to 10 moles and preferably with from 1 to 5 moles of ethylene oxide and/or propylene oxide. These esters are useful as additives to hair treatment preparations, preferably to shampoos based on anionic surfactants and, preferably, ampholytic or betaine surfactants for improving the wet combability of hair. They are added in amounts between 0.1 to 10% by weight to hair treatment preparations, and between 1 and 5% by weight to shampoos.

26 Claims, No Drawings

METHOD AND COMPOSITION FOR INCREASING WET HAIR COMBABILITY

BACKGROUND OF THE INVENTION

1. Field of the Invention

This invention relates to new phosphonic acid esters and to cosmetic hair treatment preparations containing them as additives for improving the wet combability of hair.

2. Description of Related Art

After washing with shampoos based on synthetic surfactants, the hair of the head is often in a cosmetically unsatisfactory condition. It feels dull and is difficult to comb when wet. After drying, the washed hair tends to develop a static charge which makes combing difficult and spoils the set of the combed hair.

It is known that conditioning preparations may be applied to hair after washing or shampooing. Such preparations are mostly gel-like, liquid, or emulsion-like lotions containing cationic surfactants. It is also known that certain substances may be added to normal shampoos to obtain a certain conditioning effect when the hair is washed. Examples of these substances are, for example, water-soluble proteins, protein degradation products or polycationic polymers, for example cationic cellulose derivatives. The disadvantage of cationic surfactants lies in their inadequate compatibility with anionic surfactants and their often unsatisfactory compatibility with the mucosa.

Polycationic polymers do not counteract the static charging of dry hair and, in many cases, actually increase the static charging of hair. On the other hand, the strong adsorption of these cationic polymers to the keratin fibers, particularly in the event of repeated applications, results in an accumulation of the polymers on the hair which is thus "burdened" and loses elasticity, set and body. Accordingly, there is a need for hair treatment preparations which contain additives improving the wet combability of hair and which are affected by the above-mentioned disadvantages to a lesser extent, if at all.

DESCRIPTION OF THE INVENTION

It has now been found that the wet combability of hair is distinctly improved by hair treatment preparations containing certain phosphonic acid esters as additives. These additives do not have the disadvantages attending the known additives used to improve wet combability.

Accordingly, the present invention relates to new phosphonic acid esters which may be obtained by reacting organophosphonic acids corresponding to the following general formula $R-PO_3H_2$ in which R is a linear or branched chain alkyl group containing from 2 to 22 carbon atoms or a group corresponding to general formula I, II or III below

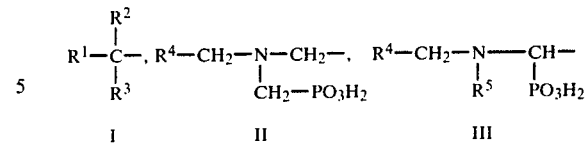

in which $R^1$ is hydrogen or a linear or branched chain alkyl group containing from 1 to 21 carbon atoms; $R^2$ is hydrogen or a $-PO_3H_2$ group; $R^3$ is hydrogen, the $-OH$ group or, in the event $R^2$ is a $-PO_3H_2$ group, then $R^3$ can also be an $-NH_2$ group; $R^4$ is the group $R^1$ or a $-PO_3H_2$ group; and $R^5$ is hydrogen or a lower alkyl group containing from 1 to 4 carbon atoms; with from 1 to 10 moles of ethylene oxide and/or propylene oxide.

The reaction of the organophosphonic acids corresponding to the formula $R-PO_3H_2$ with ethylene oxide and/or propylene oxide is carried out by the use of methods known from the literature for reactions with ethylene oxide and/or propylene oxide.

To add ethylene oxide or propylene oxide onto the acidic $-OH$ groups of the phosphono groups, it is sufficient to react the phosphonic acid with ethylene oxide and/or propylene oxide in a pressure vessel at 120° to 180° C. To add more ethylene oxide or propylene oxide onto the hydroxyethyl or hydroxypropyl groups formed or onto other, less acidic hydroxyl groups present in the molecule, it is necessary to add catalytic quantities of alkali, for example sodium alcoholate, potassium hydroxide or calcium acetate, either to the organophosphonic acid before alkoxylation or after reaction of the acidic $-OH$ groups. Another method for reacting the organophosphonic acids with ethylene oxide and/or propylene oxide is to use the organophosphonic acids in the form of an aqueous solution of their alkali salts for reaction with ethylene oxide and/or propylene oxide in the pressure vessel at 120° to 180° C.

The reaction of the organophosphonic acids with ethylene oxide results in the formation of ethylene glycol esters of the organophosphonic acids. The addition of more ethylene oxide onto the hydroxyethyl groups of the ethylene glycol esters results in the formation of polyethylene glycol esters.

The reaction with propylene oxide correspondingly results in the formation of propylene glycol esters and polypropylene glycol esters.

The organophosphonic acids $R-PO_3H_2$ suitable for use in the production of the phosphonic acid esters of the invention are known compounds or can be obtained by methods known from the literature. They include, for example, the alkane-1-phosphonic acids containing from 2 to 22 C-atoms which, according to U.S. Pat. No. 2,957,931, can be produced by the radical addition of esters of phosphorous acid onto olefins, followed by hydrolysis.

Alkane-1,1-diphosphonic acids can be obtained, for example, by alkylating methane diphosphonic acid using the process described by G. M. Kosolapoff in J. Am. Chem. Soc. 75 (1953), pages 1500–1501 for pentane-1,1-diphosphonic acid.

1-hydroxyalkane-1-phosphonic acids can be produced, for example, by reacting aldehydes with $PCl_3$ using the method described by W. Fossek in Monatshefte fuer Chemie, Vol. 7, (1886), pages 20–39.

1-hydroxyalkane-1,1-diphosphonic acids can be obtained from carboxylic acids, water and $PCl_3$ by the method described by B. Blaser, et al. in Zeitschrift fuer anorganische und allgemeine Chemie, Vo. 381 (1971), pages 247–259.

1-aminoalkane-1,1-diphosphonic acids may be produced by a process described by W. Ploeger, et al. in Zeitschrift fuer anorganische und allgemeine Chemie, Vol. 389 (1972), pages 119–128.

The same process can also be used for producing compounds in which R corresponds to general formula III, namely N-monosubstituted and N,N-disubstituted aminomethane diphosphonic acids.

Compounds in which R corresponds to general formula II can be obtained from the corresponding alkylamine, formaldehyde and phosphorous acid by the process described in German Application No. 12 14 229.

Preferred phosphonic acid esters are those compounds which can be obtained from organophosphonic acids R—$PO_3H_2$, in which R is a linear alkyl group containing from 6 or 8 to 18 C-atoms, by reaction with 1 to 5 moles of ethylene oxide and/or propylene oxide. Particularly effective compounds are, for example, the adduct of 1 mole of ethylene oxide with n-octane phosphonic acid and the adduct of 1 mole of ethylene oxide with n-octadecane phosphonic acid.

Other preferred phosphonic acid esters are those compounds which can be obtained from organophosphonic acids R—$PO_3H_2$, in which R is a group corresponding to general formula I, in which $R^1$ is a methyl group, $R^2$ is a —$PO_3H_2$ group and $R^3$ is an —OH group, by reaction with from 2 to 8 moles of ethylene oxide and/or propylene oxide. Particularly effective compounds are, for example, the adducts of 1-hydroxyethane-1,1-diphosphonic acid with from 2 to 6 moles of propylene oxide.

Other effective compounds are phosphonic acid esters of the type obtainable from organophosphonic acids R—$PO_3H_2$, in which R is a group corresponding to general formula II, in which $R^4$ is a —$PO_3H_2$ group, by reaction with from 3 to 6 moles of ethylene oxide and/or propylene oxide.

Phosphonic acid esters obtained by simultaneously or successively reacting the organophosphonic acids with ethylene oxide and propylene oxide are also suitable.

The phosphonic acid esters of the invention dissolve readily in water and in aqueous preparations. Aqueous preparations of the phosphonic acid esters of the invention are extremely effective in improving the combability and, above all, the wet combability of hair. Accordingly, even small additions of the phosphonic acid esters of the invention to hair treatment preparations, particularly to aqueous surfactant-containing preparations, are sufficient to improve the combability of wet hair. At the same time, they reduce the static charging and improve the dressability of dry hair, i.e. have a conditioning effect. The phosphonic acid esters of the invention do not lead to an accumulation on the surface of the hair with the undesirable "weighting" effect which that involves. Accordingly, the phosphonic acid esters of the invention can be added to hair treatment and hair care preparations such as, for example, shampoos, after treatment preparations, medicated preparations, dyes, bleaches, permanent-wave preparations, permanent-wave setting solutions, etc., in a wide concentration range of from about 0.1 to about 10% by weight. However, a quantity of from about 0.1 to about 5% by weight is sufficient in most cases for a satisfactory effect.

The phosphonic acid esters of the invention are also readily compatible with the typical components commonly used in the formulation of hair treatment preparations. Components such as these are, predominantly, anionic surfactants, for example alkyl sulfates and/or alkyl polyglycol ether sulfates containing from 10 to 18 C-atoms in the alkyl group and up to 12 polyglycol ether groups and/or alkyl polyglycol ether sulfo succinic acid monoesters containing from 10 to 16 C-atoms in the alkyl group and from 2 to 6 glycol ether groups. Other suitable anionic surfactants for producing the hair treatment preparations of the invention are primary and secondary linear alkane sulfonates containing from 10 to 18 C-atoms, alkene sulfonates and hydroxy alkane sulfonates, of the type obtained in the sulfonation of olefins containing from 10 to 18 C-atoms, fatty acid alkylolamide and fatty acid alkylolamide polyglycol ether sulfates, sulfated fatty acid monoglycerides, alkylpolyglycol ether carboxylates containing from 8 to 18 C-atoms in the alkyl chain and from 1 to 10 glycol ether groups, acyl sarcosines, acyl taurides and acyl isethionates containing from 8 to 18 C-atoms in the acyl group.

The anionic surfactants mentioned can be present in the form of the alkali, ammonium and alkanolammonium salts, while the alkyl sulfates and alkyl polyglycol ether sulfates can also be present in the form of the magnesium salts. They normally make up from about 2 to about 50% by weight of the hair treatment preparation.

A particularly pronounced reduction in combing resistance was observed in the case of hair treatment preparations which contain the phosphonic acid esters of the invention and, as anionic surfactants, an alkyl polyglycol ether sulfate alkali salt containing from 10 to 16 C-atoms in the alkyl group and from 2 to 4 glycol ether groups.

The phosphonic acid esters of the invention are particularly suitable for the formulation of conditioning shampoos based on anionic surfactants. In addition to from about 5 to about 20% by weight of anionic surfactants, shampoos such as these preferably contain from about 1 to about 10% by weight of ampholytic surfactants, betaine surfactants or, optionally, amine oxide surfactants. Suitable anionic surfactants are the products mentioned above, but are especially alkyl polyglycol ether sulfates.

Suitable ampholytic surfactants are, for example, N—$C_8$–$C_{18}$-alkyl-$\beta$-aminopropionic acids, N—$C_8$–$C_{18}$-alkyl-$\beta$-iminodipropionic acids or N-hydroxyethyl-N-cocosamidopropyl glycine. Suitable betaine surfactants are, for example, N-cocosalkyl-N,N-dimethyl glycine and N-cocosamidopropyl-N,N-dimethylglycine. Suitable amine oxide surfactants are, for example, N-cocosamidopropyl-N,N-dimethylamine oxide or N-cocosalkyl-N,N-di-(2-hydroxy)ethylamine oxide.

To improve wet combability and the conditioning effect, shampoos of the above type based on anionic and, preferably, ampholytic surfactants or betaine surfactants contain an addition of at least one phosphonic acid ester according to the invention, preferably in a quantity of from about 1 to about 5% by weight.

In addition to the surfactants mentioned above, the shampoos of the invention can also contain other standard auxiliaries and additives such as, for example, nonionic surfactants, small quantities of cationic surfactants, fatty acid alkanolamides, water-soluble polymers such as, for example, cellulose ethers and carboxyvinyl polymers, buffers, preservatives, dyes, perfumes, hair-cosmetic active principles, such as anti-dandruff agents, sebostatic agents, vitamins, herb extracts, etc.

The following Examples are intended to illustrate the invention without limiting it in any way.

EXAMPLES

1. Production of the phosphonic acid esters

1.1 n-octane phosphonic acid ethylene glycol ester 485 g of n-octane phosphonic acid (2.5 moles) were reacted in portions with 110 g of ethylene oxide (2.5 moles) in a pressure vessel for 2 hours at 138° C./6 bars pressure. A water-clear oil having the following characteristics was obtained:

density: $D_{20}$: 1.082
refractive index: $n_D^{20}$: 1.4547.

1.2 n-octane phosphonic acid poly(3 EO)ethylene glycol ester 291 g of n-octane phosphonic acid (1.5 moles) were introduced in a pressure vessel with 4 g of a 30% by weight solution of sodium methylate in methanol. A vacuum of approx. 10 mbar was then applied and the pressure vessel evacuated for about 30 minutes at 100° C. The temperature was then increased to 170° C. and 198 g of gaseous ethylene oxide (4.5 moles) were introduced over a period of about 2 hours under a pressure of 10 bars. Water-clear oil having the following characteristics was obtained:

density: 1.096
refractive index: 1.4593.

1.3 1-hydroxyethane-1,1-diphosphonic acid poly(4 PO)propylene glycol ester 250 g (1 mole) of the disodium salt of 1-hydroxyethane-1,1-diphosphonic acid dissolved in 192 g of water were introduced into a pressure vessel. 232 g of propylene oxide (4 moles) were introduced into the solution heated to 145° C. over a period of about 5 hours at a maximum pressure of 8 bars. A crystalline mass solidifying at room temperature was obtained. It contained approx. 71.5% by weight of dry substance and was readily soluble in water.

2. Wet combability (WC) test [%]

The effect of the additions of phosphonic acid polyglycol esters on wet combability were tested by the following method:

Approx. 11 cm long locks of brown European hair weighing 0.8 g, which had been subjected, to a single bleaching and cold-perm pretreatment, were treated for 5 minutes at 30° C. with a solution of 2.0% by weight of the phosphonic acid polyglycol ester in an aqueous surfactant solution and then thoroughly rinsed in lukewarm water (30° C.) after which excess water was stripped off. The combing resistance, i.e. the force required to draw a comb through a lock of hair, was then measured. To reduce the measurement error, the measurement was carried out 15 times with each of the products to be tested and the average value of the work integrals calculated. The measurement was carried out using a Zwick type 1402 tensile tester (Zwick company, Einsingen ueber Ulm/Donau).

The average work integral was based on the work integral obtained without active substance by treatment with the particular surfactant solution (blank value) and thus showed the improvement (or deterioration) in wet combability:

$$WC\ [\%] = \frac{\text{work integral active substance}}{\text{work integral blank value}} \cdot 100$$

Accordingly, values under 100% represent an improvement and values over 100% a deterioration in wet combability.

The results obtained with phosphonic acid esters used in hair treatment preparations in accordance with the invention are shown in Table I.

TABLE I

| No. | Phosphonic acid ester (2% AS) | Surfactant (14% AS) | WC (%) |
|---|---|---|---|
| 2.1 | n-octane phosphonic acid + 1 EO(*) | $C_{12}$-$C_{14}$—fatty alcohol + 2 EO-sulfate, Na—salt | 63 |
| 2.2 | n-octane phosphonic acid + 1 EO | lauryl sulfate, triethanolammonium salt | 77 |
| 2.3 | n-octane phosphonic acid + 1 EO | N—cocosamidopropyl-N,N—dimethyl glycine | 84 |
| 2.4 | n-octane phosphonic acid + 1 EO | $C_{12}$-$C_{14}$—fatty alcohol + 3 EO-sulfosuccinic acid monoester, Na—salt | 82 |
| 2.5 | n-octane phosphonic acid + 3 EO | $C_{12}$-$C_{14}$—fatty alcohol + 2 EO sulfate, Na—salt | 87 |
| 2.6 | n-decane phosphonic acid + 1 EO | $C_{12}$-$C_{14}$—fatty alcohol + 2 EO sulfate, Na—salt | 73 |
| 2.7 | n-octadecane phosphonic acid + 1 EO | $C_{12}$-$C_{14}$—fatty alcohol + 2 EO-sulfate, Na—salt | 53 |
| 2.8 | 1-hydroxyethane-1,1-diphosphonic acid + 2 PO(*) | $C_{12}$-$C_{14}$—fatty alcohol + 2 EO-sulfate, Na—salt | 71 |
| 2.9 | 1-hydroxyethane-1,1-diphosphonic acid + 4 PO | $C_{12}$-$C_{14}$—fatty alcohol + 3 EO-sulfate, Na—salt | 69 |
| 2.10 | 1-hydroxyethane-1,1-diphosphonic acid + 4 PO | n-cocosalkylamidopropyl-N,N—dimethyl glycine | 78 |
| 2.11 | 1-hydroxyethane-1,1-diphosphonic acid + 6 PO | $C_{12}$-$C_{14}$—fatty alcohol + 2 EO sulfate, Na—salt | 70 |
| 2.12 | 1-hydroxyethane-1,1-diphosphonic acid + 4 EO | $C_{12}$-$C_{14}$—fatty alcohol + 2 EO sulfate, Na—salt | 85 |
| 2.13 | aminotrimethylene phosphonic acid + 3 PO | $C_{12}$-$C_{14}$—fatty alcohol + 2 EO sulfate, Na—salt | 82 |

(*)EO = moles of ethylene oxide added
PO = moles of propylene oxide added

3. Application Examples

Hair shampoo formulations

| Components (% by weight) | 3.1 | 3.2 | 3.3 | 3.4 | 3.5 | 3.6 | 3.7 | 3.8 |
|---|---|---|---|---|---|---|---|---|
| ($C_{12}$-$C_{14}$)—fatty alcohol poly-(2EO)-glycol ether sulfate, Na—salt (28%) (Texapon N 25) | 50 | 40 | 45 | 40 | — | 50 | 40 | — |
| ($C_{12}$-$C_{14}$)—fatty alcohol sulfate triethanolamine salt (42%) (Texapon T 42) | — | — | — | — | 30 | — | — | — |
| Mixture of fatty alcohol ether sulfates and sulfosuccinic acid semiesters (Na—salts), 29% (Texapon SBN) | — | — | — | — | — | — | — | 40 |
| N—cocosamidopropyl-N,N—dimethyl glycine (30%) (Dehyton K) | — | — | 10 | — | — | — | 5 | — |
| N—cocosamidoethyl-N—hydroxyethyl glycine (30%) (Dehyton G) | — | — | 5 | — | — | — | — | — |
| Phosphonic acid polyglycol ester according to | | | | | | | | |
| Example 1.1 | 2 | 5 | 2.5 | 2 | 3 | — | — | — |
| Example 1.2 | — | — | — | — | — | — | — | 2 |
| Example 1.3 | — | — | — | — | — | 2.8 | 5.6 | — |
| Preservative (Bronidox L) | 0.2 | 0.2 | 0.2 | 0.2 | 0.2 | 0.2 | 0.2 | 0.2 |
| Water | ad 100 | ad 100 | ad 100 | ad 100 | ad 100 | ad 100 | ad 100 | ad 100 |

The hair shampoo formulations shown in the Table were prepared by mixing the components at room temperature (20° C.). They are clear solutions which remain clear when stored for several weeks at +5° C.

What is claimed is:

1. A hair shampoo having increased wet-hair-combability, consisting essentially of water, about 2–50% by weight of at least one anionic and/or ampholytic surfactant, and about 0.1–10% by weight, all weights based upon the total shampoo composition, of at least one phosphonic acid ester which is the reaction product of about 1–10 mols of ethylene oxide, propylene oxide, or their mixture, with 1 mol of at least one organophosphonic acid of the formula $$R-PO_3H_2$$

wherein
R is
(i) a linear or branched $C_{2-22}$-alkyl,
(ii)

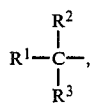

(iii)

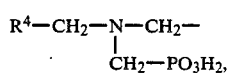

or
(iv)

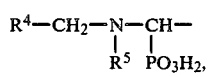

and
$R^1$ is H or a $C_{1-21}$-alkyl,
$R^2$ is H or —$PO_3H_2$,
$R^3$ is H, —OH, or —$NH_2$ if $R^2$ is —$PO_3H_2$,
$R^4$ is $R^1$ or —$PO_3H_2$, and
$R^5$ is H or a $C_{1-4}$-alkyl.

2. A method for increasing the wet hair combability imparting capacity of aqueous hair shampoos containing anionic and/or ampholytic surfactants comprising incorporating therein a wet hair combability-enhancing effective amount of at least one phosphonic acid ester which is the reaction product of about 1–10 mols of ethylene oxide, propylene oxide, or their mixture, with 1 mol of at least one organophosphonic acid of the formula $$R-PO_3H_2$$

wherein
R is
(i) a linear or branched $C_{2-22}$-alkyl,
(ii)

(iii)

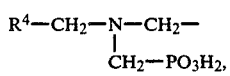

or
(iv)

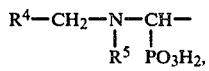

and
$R^1$ is H or a $C_{1-21}$-alkyl,
$R^2$ is H or —$PO_3H_2$,
$R^3$ is H, —OH, or —$NH_2$ if $R^2$ is —$PO_3H_2$, $R^4$ is $R^1$ or $-PO_3H_2$, and
$R^5$ is H or a $C_{1-4}$alkyl.

3. The method of claim 2 wherein R is a linear $C_{6-18}$-alkyl, and about 1-5 mols of said oxides are reacted therewith.

4. The method of claim 2 wherein R is (ii), $R^1$ is methyl, $R^2$ is $-PO_3H_2$, $R^3$ is $-OH$, and about 2-8 mols of said oxides are reacted therewith.

5. The method of claim 2 wherein R is (iii), $R^4$ is $-PO_3H_2$, and about 3-6 mols of said oxides are reacted therewith.

6. The method of claim 2 wherein said ester is the adduct of 1 mol of 1-hydroxyethane-1,1-diphosphonic acid with about 2-6 mols of propylene oxide.

7. The method of claim 2 wherein said ester is the adduct of 1 mol of 1-hydroxyethane-1,1-diphosphonic acid with 4 mols of ethylene oxide.

8. The method of claim 2 wherein said ester is the adduct of 1 mol of n-octane phosphonic acid with 1 or 3 mols of ethylene oxide.

9. The method of claim 2 wherein said ester is the adduct of 1 mol of n-decane phosphonic acid with 1 mol of ethylene oxide.

10. The method of claim 2 wherein said ester is the adduct of 1 mol of n-octadecane phosphonic acid with 1 mol of ethylene oxide.

11. The method of claim 2 wherein said ester is the adduct of 1 mol of aminotrimethylene phosphonic acid with 3 mols of propylene oxide.

12. The method of claim 2 wherein said ester is incorporated in said compositions in an amount of about 0.1-10% by weight, based upon the total weight of said compositions.

13. The method of claim 2 wherein said ester is incorporated in said compositions in an amount of about 0.1-5% by weight, based upon the total weight of said compositions.

14. The method of claim 2 further comprising incorporating in said compositions about 2-50% by weight of at least one anionic or ampholytic surfactant, based upon the total weight of said compositions, so as to afford a shampoo having enhanced wet hair combability.

15. A method for increasing the combability of wet hair comprising applying to said hair a composition consisting essentially of water and at least one phosphonic acid ester present in a wet-hair-combability-enhancing effective amount, said ester consisting essentially of the reaction product of about 1-10 mols of ethylene oxide, propylene oxide, or their mixture, with 1 mol of at least one organophosphonic acid of the formula $$R-PO_3H_2$$

wherein
R is
(i) a linear or branched $C_{2-22}$-alkyl,
(ii)

(iii)

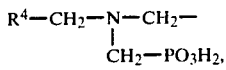

or
(iv)

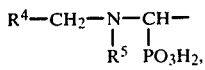

and
$R^1$ is H or a $C_{1-21}$-alkyl,
$R^2$ is H or $-PO_3H_2$,
$R^3$ is H, $-OH$, or $-NH_2$ if $R^2$ is $-PO_3H_2$,
$R^4$ is $R^1$ or $-PO_3H_2$, and
$R^5$ is H or a $C_{1-4}$-alkyl.

16. The method of claim 15 wherein R is a linear $C_{6-18}$-alkyl, and about 1-5 mols of said oxides are reacted therewith.

17. The method of claim 15 wherein R is (ii), $R^1$ is methyl, $R^2$ is $-PO_3H_2$, $R^3$ is $-OH$, and about 2-8 mols of said oxides are reacted therewith.

18. The method of claim 15 wherein R is (iii), $R^4$ is $-PO_3H_2$, and about 3-6 mols of said oxides are reacted therewith.

19. The method of claim 15 wherein said ester is the adduct of 1 mol of 1-hydroxyethane-1,1-diphosphonic acid with about 2-6 mols of propylene oxide.

20. A method for shampooing hair and simultaneously imparting thereto increased wet hair combability comprising shampooing with a composition consisting essentially of water, at least one anionic or ampholytic surfactant present in about 2-50%, based upon the total weight of the composition, and at least one phosphonic acid ester present in a wet-hair-combability-enhancing effective amount, said ester consisting essentially of the reaction product of about 1-10 mols of ethylene oxide, propylene oxide, or their mixture, with 1 mol of at least one organophosphonic acid of the formula $$R-PO_3H_2$$

wherein
R is
(i) a linear or branched $C_{2-22}$-alkyl,
(ii)

(iii)

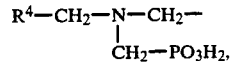

or
(iv)

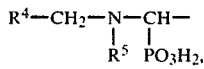

and
- $R^1$ is H or a $C_{1-21}$-alkyl,
- $R^2$ is H or $-PO_3H_2$,
- $R^3$ is H, $-OH$, or $-NH_2$ if $R^2$ is $-PO_3H_2$,
- $R^4$ is $R^1$ or $-PO_3H_2$, and
- $R^5$ is H or a $C_{1-4}$-alkyl.

21. The method of claim 20 wherein R is a linear $C_{6-18}$-alkyl, and about 1–5 mols of said oxides are reacted therewith.

22. The method of claim 20 wherein R is (ii), $R^1$ is methyl, $R^2$ is $-PO_3H_2$, $R^3$ is $-OH$, and about 2–8 mols of said oxides are reacted therewith.

23. The method of claim 20 wherein R is (iii), $R^4$ is $-PO_3H_2$, and about 3–6 mols of said oxides are reacted therewith.

24. The method of claim 20 wherein said ester is the adduct of 1 mol of 1-hydroxyethane-1,1-diphosphonic acid with about 2–6 mols of propylene oxide.

25. The method of claim 20 wherein said surfactant is at least one of:
- $C_{12-14}$-fatty alcohol+2 E.O.-sulfate, sodium salt;
- lauryl sulfate, triethanolammonium salt;
- N-cocosamidopropyl-N,N-dimethyl glycine;
- $C_{12-14}$-fatty alcohol+3 E.O.-sulfosuccinic acid monoester, sodium salt;
- $C_{12-14}$-fatty alcohol+3 E.O.-sulfate, sodium salt;
- N-cocosalkylamidopropyl-N,N-dimethyl glycine;
- $C_{12-14}$-fatty alcohol poly(2 E.O.)glycol ether sulfate, sodium salt;
- $C_{12-14}$-fatty alcohol sulfate, triethanolamine salt; or mixture of fatty alcohol ether sulfates and sulfosuccinic acid semi-esters, sodium salt.

26. The method of claim 20 wherein said surfactant is a $C_{10-16}$-alkyl poly(2–4)glycol ether sulfate, alkali salt.

* * * * *